(12) United States Patent
    Castagner et al.

(10) Patent No.: US 9,358,243 B2
(45) Date of Patent: Jun. 7, 2016

(54) **PHARMACEUTICAL COMPOUNDS FOR USE IN THE THERAPY OF *CLOSTRIDIUM DIFFICILE* INFECTION**

(71) Applicant: ETH Zurich, Zurich (CH)

(72) Inventors: Bastien Castagner, Zurich (CH); Jean-Christophe Leroux, Zurich (CH); Mattias Ivarsson, Zurich (CH); Gisbert Schneider, Zurich (CH); Anna Pratsinis, Zurich (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 14/347,649

(22) PCT Filed: Sep. 28, 2012

(86) PCT No.: PCT/EP2012/004088
    § 371 (c)(1),
    (2) Date: Mar. 27, 2014

(87) PCT Pub. No.: WO2013/045107
    PCT Pub. Date: Apr. 4, 2013

(65) Prior Publication Data
    US 2014/0235590 A1    Aug. 21, 2014

(30) Foreign Application Priority Data

Sep. 29, 2011 (EP) .................................. 11007933
Sep. 29, 2011 (EP) .................................. 11007935

(51) Int. Cl.
    *A61K 31/6615* (2006.01)
    *C07F 9/117* (2006.01)
    *C07C 305/20* (2006.01)
    *C07F 9/09* (2006.01)
    *A61K 31/255* (2006.01)
    *A61K 45/06* (2006.01)
    *A61K 31/185* (2006.01)
    *A61K 31/4164* (2006.01)
    *A61K 31/7048* (2006.01)
    *A61K 38/14* (2006.01)

(52) U.S. Cl.
    CPC ............ *A61K 31/6615* (2013.01); *A61K 31/185* (2013.01); *A61K 31/255* (2013.01); *A61K 31/4164* (2013.01); *A61K 31/7048* (2013.01); *A61K 38/14* (2013.01); *A61K 45/06* (2013.01); *C07C 305/20* (2013.01); *C07F 9/093* (2013.01); *C07F 9/117* (2013.01)

(58) Field of Classification Search
    CPC .............. A61K 31/185; A61K 31/255; A61K 31/6615; C07C 305/20; C07F 9/093; C07F 9/117
    See application file for complete search history.

(56) References Cited

U.S. PATENT DOCUMENTS 5,278,332 A * 1/1994 Siren ....................... C07F 9/117
                                                  546/12
2010/0048730 A1    2/2010 Li et al.
2012/0258936 A1* 10/2012 Savidge et al. ............... 514/143

FOREIGN PATENT DOCUMENTS

JP       S54-044901       4/1979
WO       WO 2010/049921   5/2010
WO       WO 2012/138963   10/2012

OTHER PUBLICATIONS

Xu et al. "Synthesis of phosphatase-resistant analogues of phytic acid (InsP6)" Tetrahedron Lett. 2005, 46, 8311-8314.*
G. Guttenberg et al., "Inositol Hexakisphosphate-dependent Processing of Clostridium Sordellii Lethal Toxin and Clostridium novyi—Toxin", Journal of Biological Chemisty, vol. 286, No. 17, Apr. 29, 2011, pp. 14779-14786.
Florin I et al. "Polyphosphate-mediated protection from cellular intoxication with Clostridium difficile toxin B", Biochimica et Biophysica Acta, Molecular Cell Research, vol. 805, No. 2, Oct. 12, 1984, pp. 131-136.

* cited by examiner

*Primary Examiner* — Nyeemah A Grazier
*Assistant Examiner* — Amanda L Aguirre
(74) *Attorney, Agent, or Firm* — JMB Davis Ben-David

(57) ABSTRACT

The invention relates to a compound described by a general formula (1), wherein each X independently can be $OPO_3^{2-}$, $OPSO_2^{2-}$ or $OSO_3^-$; $R^1$ comprises a solubility function such as a polyethylene glycol moiety and each X independently can be $OPO_3^{2-}$, $OPSO_2^{2-}$, $^-$ or $OSO_3^-$; and Z is an alkyl chain comprising 1 to 3 carbon and/or hetero atoms. The invention further relates to polysulfate derivatives or mixed polyphosphate/sulphate derivatives of six-membered cyclic polyols for use in the therapy of infection by *Clostridium difficile*.

3 Claims, 6 Drawing Sheets

A

B

PHARMACEUTICAL COMPOUNDS FOR USE IN THE THERAPY OF *CLOSTRIDIUM DIFFICILE* INFECTION

CROSS-REFERENCE TO RELATED APPLICATIONS

This is the U.S. National Stage of International Application No. PCT/EP2012/004088, filed Sep. 28, 2012, which was published in English under PCT Article 21(2), which in turn claims the benefit of European Patent Application No. 11007935.7, filed Sep. 29, 2011 and European Patent Application No. 11007933.2, filed Sep. 29, 2011.

The present invention relates to enteric activators of *Clostridium difficile* toxin, particularly polyphosphate derivatives, polysulfate derivatives or mixed polyphosphate/sulphate derivatives of six-membered cyclic polyols.

*Clostridium difficile* is a species of Gram-positive bacteria that causes severe diarrhoea in human patients. *C. difficile* infection (CDI) typically affects patients under antibiotic treatment since the bacterium is only able to colonize the colon of patients with depleted bacterial flora. The emergence of antibiotic-resistant strains of *C. difficile* causes increasingly severe morbidity and mortality due to the spread of new, more virulent strains, with recent outbreaks in North America and Europe.

*C. difficile* asymptomatically colonizes 2-5% of the human adult population. The bacteria form spores, which are difficult to neutralize by common methods of disinfection. As a result, *C. difficile* infections are a common result of prolonged stays in hospitals; the pathogen is considered the leading cause of hospital-associated diarrhoea in the USA.

Current therapy of choice is oral application of metronidazole or, in case of failure of the former, vancomycin. Since clinical symptoms of CDI are caused by two toxic proteins secreted by *C. difficile* in the colon, rather than by the presence of the bacteria itself, efforts have been made recently to target these toxins (e.g. employing polymeric binders), but have so far failed in clinical trials.

*C. difficile* enterotoxin (toxin A, TcdA) and cytotoxin (toxin B, TcdB) are the main contributors to the symptoms of disease (for a toxin biology review, see Voth and Ballard, *Clinical Microbiology Reviews* 2005, 18, 247-263). In brief, both toxins are composed of four domains, a first domain mediating the attachment of the toxin to cells; a second one facilitating translocation into the cytosol; a third domain causing the cleavage of the toxic domain by autoproteolysis, and finally the toxic domain or "warhead" itself, which causes the physiological effects of the toxin in the affected cell.

Reineke et al. (*Nature* 2007, 446, 415) identified myo-inositol hexakisphosphate (IP6) as the natural trigger of TcdA/TcdB autoprocessing in the cell cytosol. Egerer et al. (*PLoS Pathog.* 2010, 6, e1000942) and Shen et al. (*Nat. Struct. Mol. Biol.* 2011, 18, 364) suggested targeting the IP6-induced autoprocessing mechanism as a means of therapeutic intervention against toxin-mediated pathogenicity.

Kreimeyer et al. suggested using IP6 pharmaceutically to intervene in CDI (*Naunyn-Schmiedeberg's Arch. Pharmacol.* 2011, 383, 253). However, this approach is not feasible as the presence of high calcium concentrations in the colon precipitates IP6 and prevents it from being active.

Thus, the objective of the present invention is to provide improved treatment options for patients suffering from CDI. This objective is attained by the subject-matter of the independent claims.

DEFINITIONS

The term alkyl or alkyl group in the context of the present invention signifies a saturated hydrocarbon moiety, which may be linear, branched, cyclic or cyclic with linear or branched side chains. The term alkyl includes partially unsaturated hydrocarbons such as propenyl. Examples are methyl, ethyl, n- or isobutyl, n- or cyclohexyl. The term alkyl may extend to alkyl groups linked or bridged by hetero atoms. Hetero atoms in the context of the present invention are nitrogen (N), sulfur (S) and oxygen (O).

A $C_1$-$C_3$ alkyl in the context of the present invention signifies a saturated linear or branched hydrocarbon having 1, 2, or 3 carbon atoms, wherein one carbon-carbon bond may be unsaturated and one $CH_2$ moiety may be exchanged for oxygen (ether bridge). Non-limiting examples for a $C_1$-$C_3$ alkyl are methyl, ethyl, propyl, prop-2-enyl and prop-2-inyl.

A $C_1$-$C_5$ alkyl in the context of the present invention signifies a saturated linear or branched hydrocarbon having 1, 2, 3, 4 or 5 carbon atoms, wherein one or two carbon-carbon bond may be unsaturated and one $CH_2$ moiety may be exchanged for oxygen (ether bridge). Non-limiting examples for a $C_1$-$C_5$ alkyl include the examples given for $C_1$-$C_3$ alkyl above, and additionally n-butyl, 2-methylpropyl, tert-butyl, 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, but-3-enyl, but-3-inyl and pent-4-inyl.

A $C_3$-$C_{10}$ alkyl in the context of the present invention signifies a saturated linear or branched hydrocarbon having 3, 4, 5, 6, 7, 8, 9 or 10 carbon atoms, wherein 1, 2 or 3 carbon-carbon bonds may be unsaturated and one $CH_2$ moiety may be exchanged for oxygen (ether bridge).

A monosaccharide in the context of the present invention signifies a sugar comprising three, four, five, six or seven carbon atoms. Examples are glyceraldehyde (C3), erythrose or threose (C4), arabinose, ribose or xylose (C5) glucose, mannose, galactose or fructose (C6) or sedoheptulose (C7). The sugar alcohols and amino sugars of C3, C4, C5, C6 and C7 monosaccharides are included in the group of monosaccharides according to the definition used herein.

An oligosaccharide is a molecule consisting of two to ten of the same or different monosaccharides according to the above definition. A polysaccharide comprises more than ten monosaccharides.

A polymer of a given group of monomers is a homopolymer (made up of a multiple of the same monomer); a copolymer of a given selection of monomers is a heteropolymer constituted by monomers of at least two of the group.

The invention is based on a novel design of small-molecule analogues of IP6 that are provided as an oral therapy to trigger the cleavage of the toxin in the colon lumen, thereby detaching the warhead before it reaches its destination, and rendering it harmless. Since IP6 itself cannot be used for this purpose because it is not soluble at the high calcium concentrations found in the colon lumen, the present invention provides new analogues of IP6 with improved solubility.

According to a first aspect of the invention, a pharmaceutical compound characterized by a general formula (1) is provided, (1)

wherein
R$^1$ is or comprises a solubility function R$^2$ selected from the group including
  a polyethylene glycol;
  a monosaccharide, oligosaccharide or polysaccharide,
  a polyglycerol, for example a polyglycerol described by the formula ((R$^3$—O—(CH$_2$—CHOH—CH$_2$O)$_n$—) with R$^3$ being hydrogen, methyl or ethyl, and n having a value from 3 to 200, or a branched or hyperbranched polyglycerol, such as may be described by the formula (R$^3$—O—(CH$_2$—CHOR$^5$—CH$_2$—O)$_n$—) with R$^5$ being hydrogen or a glycerol chain and R$^3$ being hydrogen, methyl or ethyl;
  a polymer or copolymer comprising a plurality of any of the monomers hydroxypropyl methacrylate (HPMA), hydroxyethyl methacrylate (HEMA), vinyl alcohol (VA), vinyl pyrrolidone (VP), N-isopropyl acrylamide (NIPAM) and/or PEG methacrylate (PEGMA)

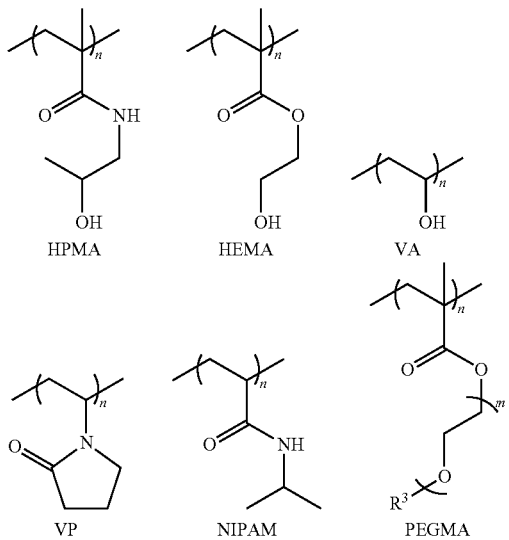

with n and m independently having a value from 3 to 200;
  a poly(styrene-co-maleic acid/anhydride);
  a C$_3$-C$_{10}$ alkyl comprising at least three substituent functions independently selected from the group including an amine-, hydroxy-, thiol-, carboxylic acid, carboxylic amide, sulfonic acid or sulfonamide function, and
each X independently is selected from OPO$_3^{2-}$, OPSO$_2^{2-}$, or OSO$_3$,
Z is an alkyl chain comprising 1 to 3 carbon and/or hetero atoms, optionally comprising a group X, wherein X has the meaning defined above.

An amine function is a function NR'R", with R' and R" selected independently from hydrogen and C$_1$-C$_5$ alkyl. In some embodiments, R' and R" are selected from hydrogen and C$_1$-C$_3$ alkyl. A hydroxy function is OH. A thiol function is SH. A carboxylic acid function is COOH or its anion, COO$^-$. A carboxylic amide is CONR'R", with R' and R" independently having the meanings indicated above. A sulfonic acid is SO$_3$H. A sulfonic acid amide is SO$_2$NR'R", with R' and R" independently having the meanings indicated above.

In some embodiments, said polyethylene glycol is described by a formula (R$^3$—(O—CH$_2$—CH$_2$)$_n$—) with R$^3$ being hydrogen, methyl or ethyl, and n having a value from 3 to 200. In some embodiments, n has a value from 3 to 20. In some embodiments, n has a value from 10 to 30. In some embodiments, n has a value from 9 to 45. In some embodiments, said polyethylene glycol is a branched polyethylene glycol.

In some embodiments, R$^1$ comprises an ether, thioether, carboxylic ester, amine, carboxylic amide, urea, sulfonamide, phosphoramide, phosphate ester, phosphorothioate, alkyl, triazole or carbamate function, or a combination of any of the preceding groups, which links R$^2$ to the molecule.

In some embodiments, R$^1$ is a CH$_2$, a CH$_2$CH$_2$, a CHX, a CHX—CH$_2$, a CH$_2$CHX, a CHX—CHX, CH$_2$—O or a CHX—O group linking R$^2$ to the molecule.

In some embodiments, formula (1) describes a five-membered, six-membered or seven-membered alkyl ring and R$^1$ is covalently attached to one of the carbon atoms forming the ring.

In some embodiments, R$^1$ is attached to a CH group forming the ring. According to another embodiment, R$^1$ is attached to a CX group forming the ring (that is, a ring carbon can be represented by CXR$^1$, wherein X and R$^1$ have the meanings indicated above).

In some embodiments, R$^2$ is a C$_3$, C$_4$, C$_5$, C$_6$, C$_7$, or C$_8$ alkyl group comprising three, four, five, six, seven or eight substituent functions independently selected from the group including an amine-, hydroxy-, thiol-, carboxylic acid, carboxylic amide, sulfonic acid or sulfonamide function.

In some embodiments, R$^2$ is a polyglycerol described by the formula ((R$^3$—O—(CH$_2$—CHOH—CH$_2$O)$_n$—) with R$^3$ being hydrogen, methyl or ethyl, and n having a value from 3 to 200. In some alternatives of these embodiments, n has a value from 3 to 20. In some alternatives of these embodiments, n has a value from 10 to 30. In some alternatives of these embodiments, n has a value from 9 to 45.

In some embodiments, R$^2$ is a branched polyglycerol described by the formula (R$^3$—O—(CH$_2$—CHOR$^5$—CH$_2$—O)$_n$—) with R$^5$ being hydrogen or a linear glycerol chain described by the formula (R$^3$—O—(CH$_2$—CHOH—CH$_2$—O)$_n$—) and R$^3$ being hydrogen, methyl or ethyl.

In some embodiments, R$^2$ is a hyperbranched polyglycerol described by the formula (R$^3$—O—(CH$_2$—CHOR$^5$—CH$_2$—O)$_n$—) with R$^5$ being hydrogen or a glycerol chain described by the formula (R$^3$—O—(CH$_2$—CHOR$^6$—CH$_2$—O)$_n$—), with R$^6$ being hydrogen or a glycerol chain described by the formula (R$^3$—O—(CH$_2$—CHOR$^7$—CH$_2$—O)$_n$—), with R$^7$ being hydrogen or a linear glycerol chain described by the formula (R$^3$—O—(CH$_2$—CHOH—CH$_2$—O)$_n$—) and R$^3$ being hydrogen, methyl or ethyl.

Hyperbranched glycerol and methods for its synthesis are described in Oudshorn et al., Biomaterials (2006), 27, 5471-5479; Wilms et al., Acc. Chem. Res. (2010) 43, 129-41, and references cited therein.

In some embodiments, R$^2$ is a polymer or copolymer comprising a plurality of any of the monomers hydroxypropyl methacrylate (HPMA), hydroxyethyl methacrylate (HEMA), vinyl alcohol (VA), vinyl pyrrolidone (VP), N-isopropyl acrylamide (NIPAM) and/or PEG methacrylate (PEGMA)

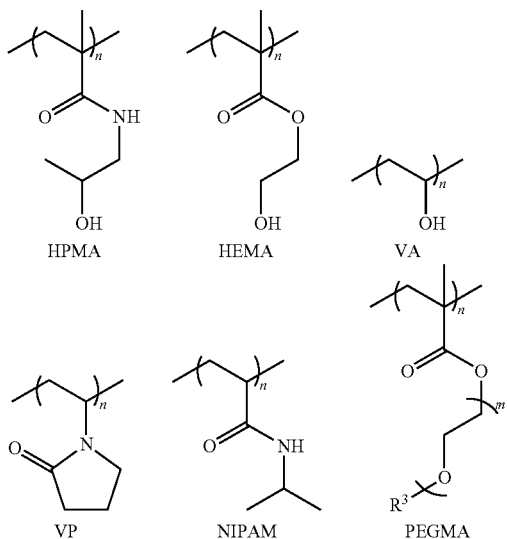

with n having a value from 3 to 200 and m having a value from 3 to 200. In some alternatives of these embodiments, n has a value from 3 to 20 and m has a value from 3 to 200. In some alternatives of these embodiments, n has a value from 10 to 30 and m has a value from 3 to 200. In some alternatives of these embodiments, n has a value from 20 to 50 and m has a value from 3 to 200. In some alternatives of these embodiments, n has a value from 3 to 200 and m has a value from 3 to 20. In some alternatives of these embodiments, n has a value from 3 to 200 and m has a value from 10 to 30. In some alternatives of these embodiments, n has a value from 3 to 200 and m has a value from 20 to 50.

In embodiments wherein the solubility function is attached to the compound directly, $R^1$ equals (is) $R^2$.

In some embodiments, Z is $CH_2$, CHX, $CHR^1$, $CXR^1$, $CH_2$—$CH_2$, $CH_2$—CHX, CHX—CHX, $CHR^1$—CHX, $CXR^1$—CHX, $CHR^1$—$CH_2$, $CXR^1$—$CH_2$, $CHR^1$—CHOH, $CH_2$—$CH_2$—$CH_2$, $CH_2$—O—$CH_2$, CHOH—$CH_2$—$CH_2$, CHOH—CHOH—$CHR^1$, CHOH—$CHR^1$—CHOH, CHX—$CH_2$—$CH_2$, $CH_2$—CHX—$CH_2$, CHX—CHX—$CH_2$, CHX—$CH_2$—CHX or CHX—$CHR^1$—CHX.

The solubility function provides for the solubility of the molecule in aqueous solution in the presence of 10 mmol/l $Ca^{2+}$. The molecule according to the invention has a higher solubility than IP6 in concentrations of calcium higher than 1 mmol/l; according to a preferred embodiment, the solubility of the molecule of the invention is above 10 μmol/l.

In some embodiments, the pharmaceutical compound according to the invention is characterized by a general formula (2)

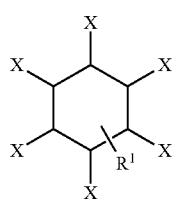
(2)

wherein X and $R^1$ have the meaning outlined above.

In some embodiments, the compound is characterized by a general formula (3), wherein X and $R^1$ have the meaning outlined above:

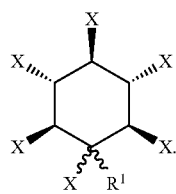
(3)

In some embodiments, the compound of the invention comprises a five- to seven-membered ring, wherein at least four ring members can be described by a formula CH—X, and one ring member can be described by a formula Y—$R^1$, with Y being CH or N, and $R^1$ and each X independently having the meaning defined above. In some embodiments, only one ring member can be described by a formula Y—$R^1$. In some embodiments, the compound of the invention has a five-membered circular structure, with four members of the ring described by a formula CH—X and one member described by a formula Y—$R^1$, with X, Y and $R^1$ as defined above. In some embodiments, the compound of the invention has a six-membered circular structure, with five members of the ring described by a formula CH—X and one member described by a formula Y—$R^1$, with X, Y and $R^1$ as defined above. In some embodiments, the compound of the invention has a seven-membered circular structure, with six members of the ring described by a formula CH—X and one member described by a formula Y—$R^1$, with X, Y and $R^1$ as defined above.

In some embodiments, the compound of the invention is described by a formula (4). In some embodiments, it is described by formula (5) or formula (6).

In some embodiments, such circular molecule according to the invention can be described by a general formula

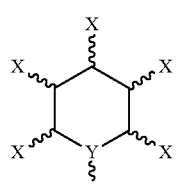
(4)

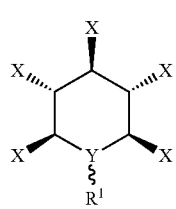
(5)

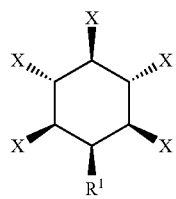
(6)

wherein each X (independently), Y and $R^1$ have the meaning defined above.

In one embodiment, (6) comprises a poly(ethylene glycol) $PEG_{400}$ as solubility function, with $R^1$ being $CH_3(OCH_2$—$CH_1)_9$—O—:

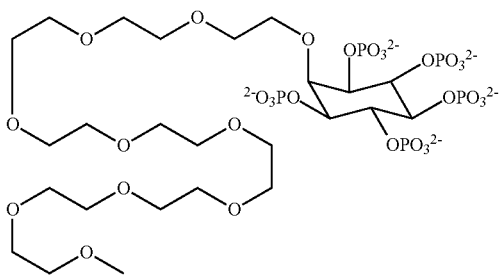

(7)

myo-inositol-pentakisphosphate-2-PEG(400) (7) is the PEG$_{400}$-analogue of myo-inositol hexakisphosphate. (7) has proved to have an improved ability to cleave TcdB CPD in the presence of calcium.

Another embodiment relates to the PEG$_{2000}$ analogue to (7), i.e. a PEG with approximately 45 ethylene glycol monomers.

Another embodiment relates to an analogue to scyllo-inositol hexakisphosphate as described by formula (8)

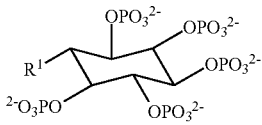

(8)

wherein R$^1$ has the same meaning as outlined above. In some embodiments, the compound of the invention can be described by formula (8) and R$^1$ is a poly(ethylene glycol) moiety.

The solubility function, a poly(ethylene glycol) (PEG) chain shown here as a non-limiting example, is attached to the molecule to render it soluble in the colon lumen, at the concentrations of calcium present therein.

According to a second aspect of the invention, an inositol-hexakissulfate (inositol hexasulfate; IS6) is provided for therapy or prevention of CDI. A particularly preferred embodiment is myo-(11) or scyllo-inositolhexakissulfate (12).

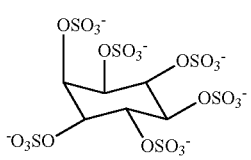

(11)

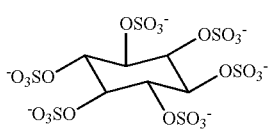

(12)

Although comparable to IP6 in structure and charge density, the present invention surprisingly shows that in the presence of calcium, IS6 is much more active than IP6 (see FIG. 4).

Inositol hexakissulphate is available commercially (CAS No. 28434-25-5; inter alia, Santa Cruz Biotechnology, Santa Cruz, Calif., USA).

According to a third aspect of the invention, a pharmaceutical compound characterized by a general formula (15) is provided,

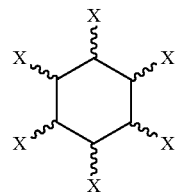

(15)

wherein each X independently is selected from OPO$_3^{2-}$, OPSO$_2^{2-}$, or OSO$_3^-$, with the proviso that not all X are OPO$_3^{2-}$ and not all X are OPO$_3^-$.

According to a fourth aspect of the invention, the compound characterized in the previous paragraph by formula (15) is provided for use as a medicament, particularly for use in the prevention or therapy of infections by *Clostridium difficile*.

In some embodiments, the compound according to this third aspect of the invention is characterized by a general formula (15a) or (15b), wherein X has the meaning outlined above:

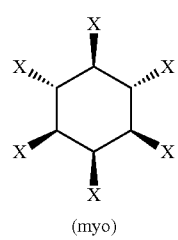

(15a)

(myo)

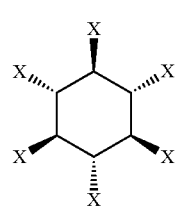

(15b)

(scyllo)

In some embodiments, the compound according to this third aspect of the invention is characterized by the general formula (16a) or (16b),

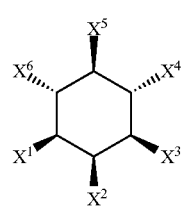

(16a)

-continued

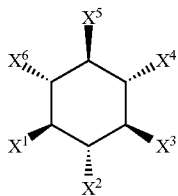

(16b)

wherein
a) $X^2$ is $OPO_3^-$, and $X^1$, $X^3$, $X^4$, $X^5$ and $X^6$ are independently selected from $OPO_3^{2-}$, $OPSO_3^{2-}$ or $OSO_3^-$,
b) $X^1$, $X^3$ and $X^5$ are $OPO_3^{2-}$ and $X^2$, $X^4$ and $X^6$ are $OSO_3^-$ (Compound 16a-b or 16b-b),
c) $X^1$, $X^3$ and $X^5$ are $OPO_3^-$ and $X^2$, $X^4$ and $X^6$ are $OPO_3^{2-}$ (Compound 16a-c or 16b-c),
d) $X^4$, $X^5$ and $X^6$ are $OPO_3^-$ and $X^1$, $X^2$ and $X^3$ are $OPO_3^{2-}$ (Compound 16a-d or 16b-d),
e) $X^4$, $X^5$ and $X^6$ are $OPO_3^{2-}$ and $X^1$, $X^2$ and $X^3$ are $OSO_3^-$ (Compound 16a-e or 16b-e),
f) $X^2$ and $X^5$ are $OPO_3^{2-}$ and $X^1$, $X^3$, $X^4$, and $X^6$ are $OPO_3^-$ (Compound 16a-f or 16b-f),
g) $X^2$ and $X^5$ are $OPO_3^-$ and $X^1$, $X^3$, $X^4$, and $X^6$ are $OPO_3^{2-}$ (Compound 16a-g or 16b-g),
h) $X^2$ and $X^3$ are $OPO_3^{2-}$ and $X^1$, $X^4$, $X^5$, and $X^6$ are $OPO_3^-$ (Compound 16a-h or 16b-h), or
i) $X^2$ and $X^3$ are $OPO_3^-$ and $X^1$, $X^4$, $X^5$, and $X^6$ are $OPO_3^{2-}$ (Compound 16a-i or 16b-i).

The compounds defined above can be synthesized according to standard methods. The synthesis of compound 16a-b is described in the examples of the present invention.

According to another aspect of the invention, a compound according to any of the above aspects of the invention, in the broadest definition given, or as specified in any of the embodiments, is provided for use as a medicament.

According to yet another aspect of the invention, a compound according to any of the above aspects of the invention, in the broadest definition given, or as specified in any of the embodiments, is provided for use in the treatment or prevention of C. difficile infection.

A compound according to the invention may be given to a patient already diagnosed with CDI, or to a patient being suspected of suffering from CDI. Alternatively, the compound may be used as a prophylactic for patients that are at risk of contracting the infection, such as patients under antibiotic treatment in hospital settings. The compounds according to the invention are simple to synthesize, resistant to degradation in the gastro-intestinal tract and unlikely to be absorbed into the bloodstream, thus avoiding potential side effects. The compounds according to the invention do not need to penetrate mammalian or bacterial membranes to be active, which makes them more effective in vivo. In addition, the compounds according to the invention are unlikely to exert selective pressure on the bacteria and therefore avoid problems related to resistance.

According to yet another aspect of the invention, a pharmaceutical composition for use in a method for the prevention or treatment of C. difficile infection is provided, comprising a compound according to any of the above aspects of the invention.

Preferred pharmaceutical compositions comprise from approximately 1% to approximately 95% active ingredient, preferably from approximately 20% to approximately 90% active ingredient.

A pharmaceutical composition according to the above aspects of the invention can be administered alone or in combination with one or more other therapeutic agents. A combination therapy may take the form of fixed combinations of the compound of the invention and one or more other antibiotic agents. Administration may be staggered; alternatively drugs may be given independently of one another, or as a fixed combination.

According to a preferred embodiment, a pharmaceutical composition comprises a compound of the invention according to any of the above aspects of the invention, and additionally metronidazole, vancomycin and/or fidaxomicin.

According to yet another aspect of the invention, a dosage form is provided comprising a compound according to any of the above aspects of the invention. A peroral formulation, particularly a tablet, syrup, solution, capsule or powder is preferred.

According to a preferred embodiment, such a dosage form additionally comprises an antibiotically active compound, such as (by way of non-limiting example) metronidazole, vancomycin or fidaxomicin.

According to yet another aspect of the invention a treatment regime is provided for the prevention and treatment of CDI, comprising the administration of a compound according to the invention. Administration may be effected by any of the means described herein.

Also within the scope of the present invention is a method for the prevention or treatment of CDI, comprising the administration a compound according to the invention to a subject in need thereof.

Similarly, a compound according to the invention is provided for the manufacture of a medicament for the prevention and treatment of CDI. Medicaments according to the invention are manufactured by methods known in the art, especially by conventional mixing, coating, granulating, dissolving or lyophilizing.

Wherever alternatives for single features such as $R^1$, $R^2$, X etc. are laid out herein as "embodiments", it is to be understood that such alternatives may be combined freely to form discrete embodiments of the entire molecule provided as such or for use in a method or medical indication herein. Thus, any of the alternative embodiments for $R^1$ may be combined with any of the alternative embodiments of Z or any of the ring structures provided in the formulae mentioned herein.

SHORT DESCRIPTION OF THE FIGURES

EXAMPLES

1. Synthesis of Compound (7)

Figure 3:
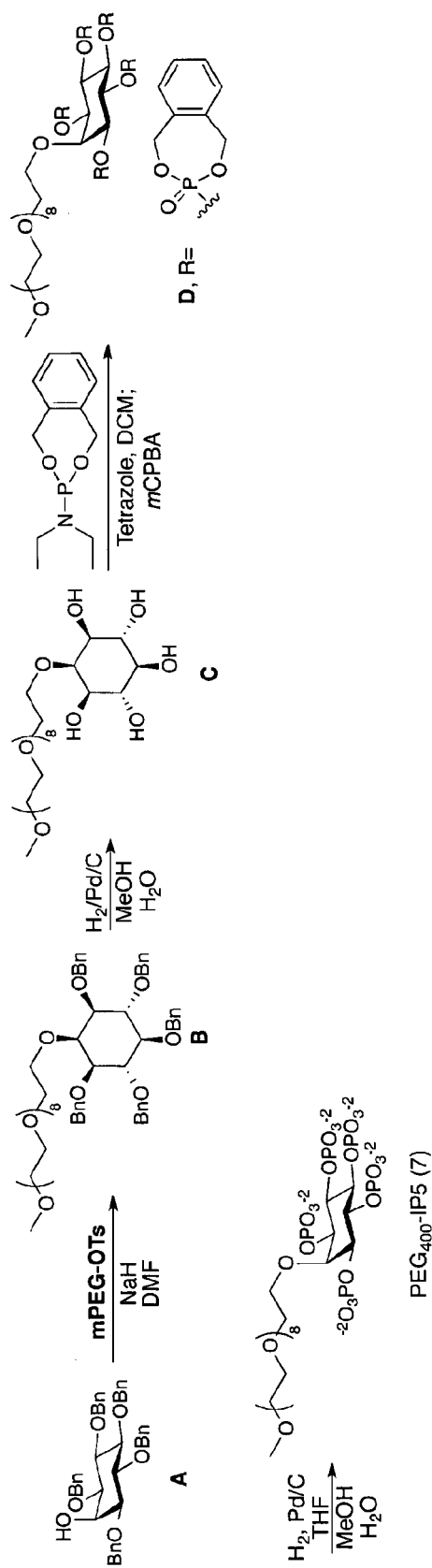
FIG. 3 shows the synthesis of compound 7.
Figure 4:
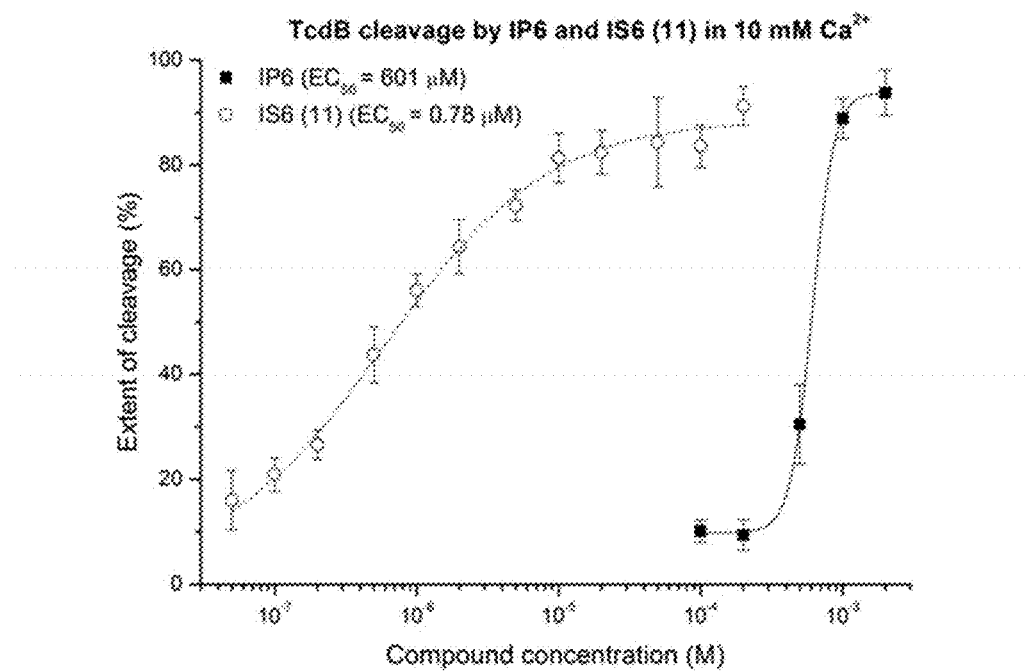
FIG. 4 shows the concentration dependence of cleavage of TcdB cysteine protease domain in the presence of 10 mM $Ca^{2+}$ for activator compound (11); activator data shown as empty circles; IP6 control as black squares.
Figure 5:
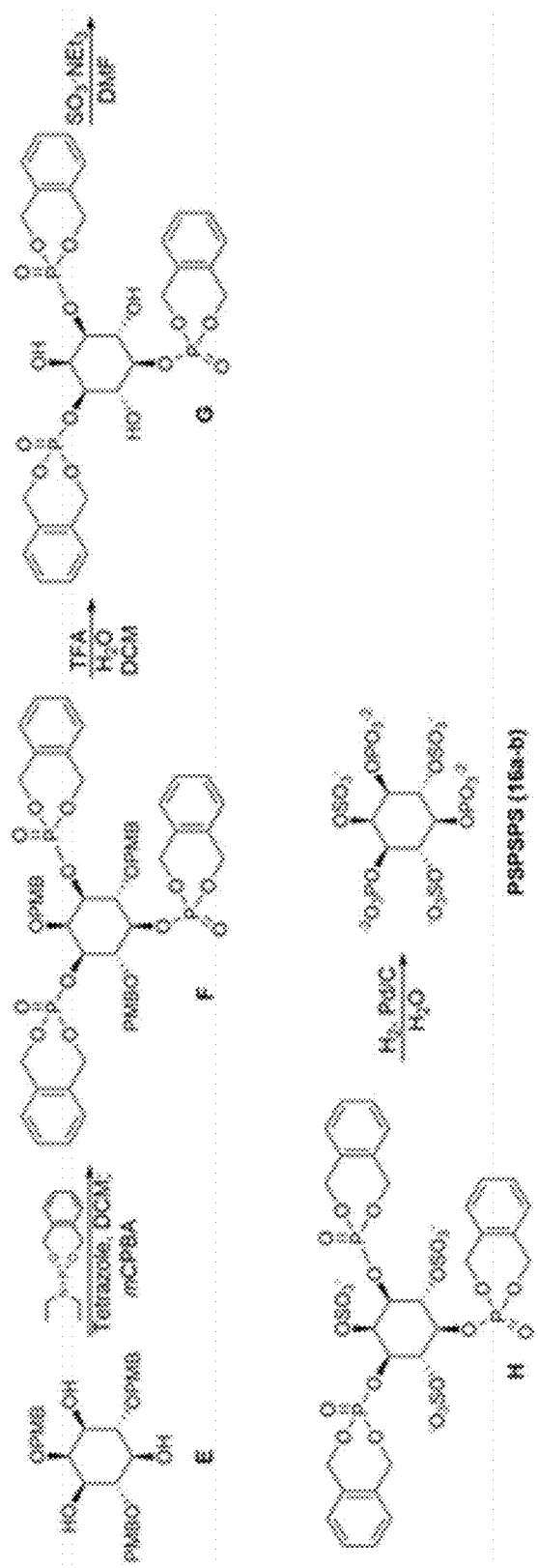
FIG. 5 shows the synthesis of compound (16a-b).
Figure 6:
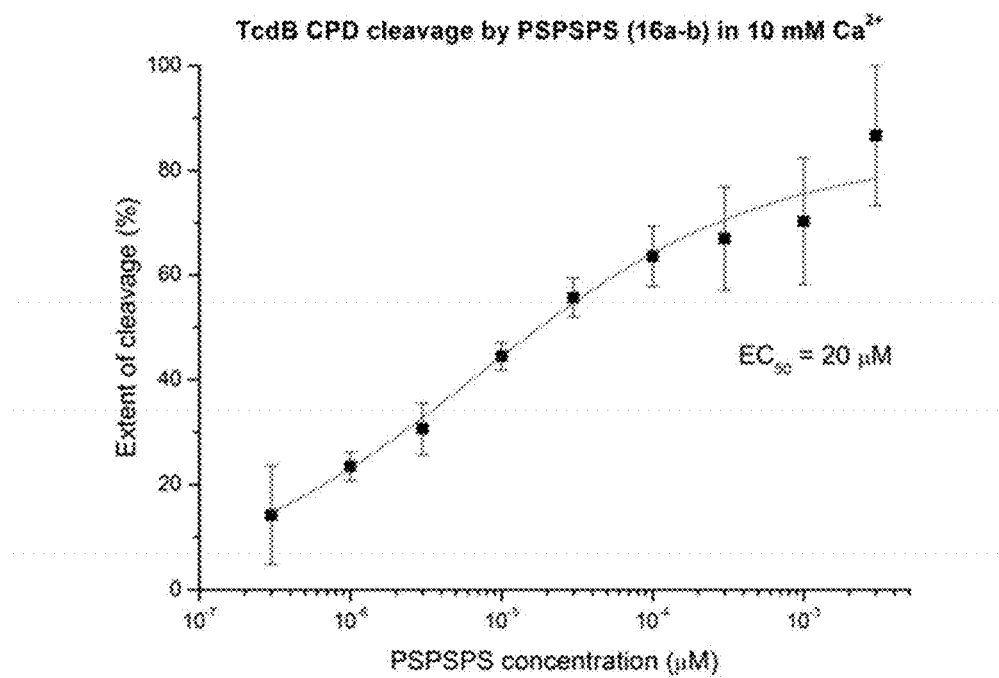
FIG. 6 shows the concentration dependence of cleavage of TcdB cysteine protease domain in the presence of 10 mM $Ca^{2+}$ for activator compound (16a-b).

The synthesis followed the sequence depicted in FIG. 3.

Compound B: To a suspension of sodium hydride (4.3 mmol, 103.7 mg) in 10 mL dimethylformamide (DMF) was added a solution of compound A [Martin, S. F. et al., *J. Org. Chem.* 1994, 59, 4805] (2.16 mmol, 1363 mg) in DMF (10 mL) dropwise. When the addition was complete the mixture was stirred for 30 min at room temperature, followed by addition of MeO-PEG-OTs (OTs being toluenesulfonate) (3.2 mmol, 1.64 g in 10 mL DMF). The reaction was allowed to stir overnight, then quenched with water (5 mL). The mixture was extracted with dichloromethane (DCM). The solvent was evaporated and the residue was chromatographed on silica gel with six 100 mL portions of 20:80; 30:70; 40:60; 60:40; 80:20; 100:0 of ethylacetate:hexanes. The chromatography resulted in the fractionation of product with different PEG sizes, including compound B with an average of 9 PEG units. $^1$H NMR (400 MHz; CDCl$_3$): δ 7.29-7.13 (m, 25H), 4.83 (d, J=10.8 Hz, 2H), 4.79 (s, 2H), 4.74 (d, J=10.8 Hz, 2H), 4.63 (d, J=11.7 Hz, 2H), 4.59 (d, J=11.6 Hz, 2H), 3.97-3.88 (m, 5H), 3.64-3.42 (m, 31H), 3.38 (t, J=9.2 Hz, 1H), 3.29-3.25 (m, 5H).

Compound C: Compound B was dissolved in a mixture of tetrahydrofuran (THF, 4 mL), methanol (7 mL) and water (3 mL), followed by addition of excess 10% palladium on charcoal. The mixture was placed under a hydrogen atmosphere and stirred overnight at room temperature. The reaction mixture was then purged with nitrogen, filtered and the solvent evaporated. The crude mixture was purified on a reverse phase cartridge (Sep-Pak, Waters, 1 g, C$_{18}$, Cat.# WAT 036905) by eluting with 10 mL water. All fractions (1.5 ml) were lyophilized and analyzed by $^1$H NMR analysis. $^1$H NMR (400 MHz; D$_2$O): δ 3.96-3.94 (m, 2H), 3.89 (t, J=2.8 Hz, 1H), 3.78-3.69 (m, 28H), 3.69-3.60 (m, 5H), 3.56 (dd, J=10.0, 2.8 Hz, 2H), 3.40 (s, 3H), 3.25 (t, J=9.2 Hz, 1H).

Compound D: Compound C (0.2 mmol, 119 mg) was suspended in tetrazole (3.630 mmol, 8.1 mL, 0.45 M in CH$_3$CN) and DCM (10 mL) then N,N-diethyl-1,5-dihydro-2,4,3-benzodioxaphosphepin-3-amine (1.8 mmol, 434 mg) was added and the mixture was stirred at room temperature overnight. The mixture was then cooled to −10° C. and a solution of meta-chloroperoxybenzoic acid (mCPBA, predried over Na$_2$SO$_4$, 4.8 mmol, 1189 mg) in DCM (2 mL) was added. The mixture was allowed to stir at −10° C. for an additional 10 min, and then it was brought to room temperature and stirred for 1 hour. The mixture was washed with dilute sodium sulfite and extracted with DCM. The organic layers were dried with Na$_2$SO$_4$, filtered and concentrated. The residue was chromatographed on silica gel with a gradient of 1-5% methanol in DCM. $^1$H NMR (400 MHz; CDCl$_3$): δ 7.41-7.27 (m, 18H), 7.21 (dd, J=6.9, 1.7 Hz, 2H), 5.59-5.51 (m, 6H), 5.44 (t, J=14.2 Hz, 2H), 5.37-5.29 (m, 6H), 5.25-4.95 (m, 10H), 4.74 (ddd, J=9.9, 7.6, 2.1 Hz, 2H), 4.61 (t, J=2.2 Hz, 1H), 4.03 (t, J=4.9 Hz, 2H), 3.68-3.50 (m, 22H), 3.48 (dd, J=6.1, 4.0 Hz, 2H), 3.40-3.34 (m, 7H). $^{13}$C NMR (101 MHz; CDCl$_3$): δ 135.78, 135.72, 135.4, 135.14, 134.99, 129.38, 129.27, 129.26, 129.22, 129.14, 129.11, 128.96, 128.95, 77.6, 76.05, 76.01, 73.8, 71.9, 70.67, 70.60, 70.57, 70.54, 70.53, 70.49, 70.38, 70.34, 70.29, 69.46, 69.39, 69.33, 69.24, 69.16, 69.01, 68.95, 59.0

Compound (7): Compound D was dissolved in a mixture of THF (1 mL), methanol (1.5 mL) and water (2 mL), followed by addition of excess 10% palladium on charcoal. the mixture was placed under an hydrogen atmosphere and stirred overnight at room temperature. The mixture was then purged with nitrogen, filtered and concentrated. The compound was brought at pH 7 by addition of dilute aqueous NaOH (170 µl, 0.1M). The residue was purified on a sephadex column (PD-10, GE Healthcare, Sephadex G-25 M, cat.#17-0851-01) by eluting with 10 ml of water. All fractions (1.5 mL) were lyophilized and analyzed by $^1$H NMR. The fractions containing product were purified further on a reverse phase cartridge (Sep-Pak, Waters, 1 g, Cis, cat.# WAT 036905) by eluting with 10 mL water. All fractions (1.5 ml) were lyophilized and analyzed by $^1$H NMR analysis. $^1$H NMR (400 MHz; D$_2$O): δ 4.44 (q, J=9.4 Hz, 2H), 4.20 (s, 1H), 4.16-4.10 (m, 3H), 4.06 (t, J=4.7 Hz, 2H), 3.83-3.63 (m, 26H), 3.40 (s, 3H). $^{31}$P NMR (162 MHz; D$_2$O): δ 1.5, 1.2, 0.8

2. Determination of EC50 in Presence of 10 mM Ca$^{2+}$

The compound to be tested was added to a recombinant His-tagged cysteine protease domain of *C. difficile* toxin B of SEQ ID 1 in presence of 10 mM Ca$^{2+}$ in 100 mM Tris pH7.4 and incubated for 2 h at 37° C. Cleaved protein fragments were separated by SDS-PAGE and visualized by Coomassie staining. The extent of cleavage quantified from protein band intensities using the ImageJ software package. Signals were normalized to cleavage of positive and negative controls.

Figure 1:
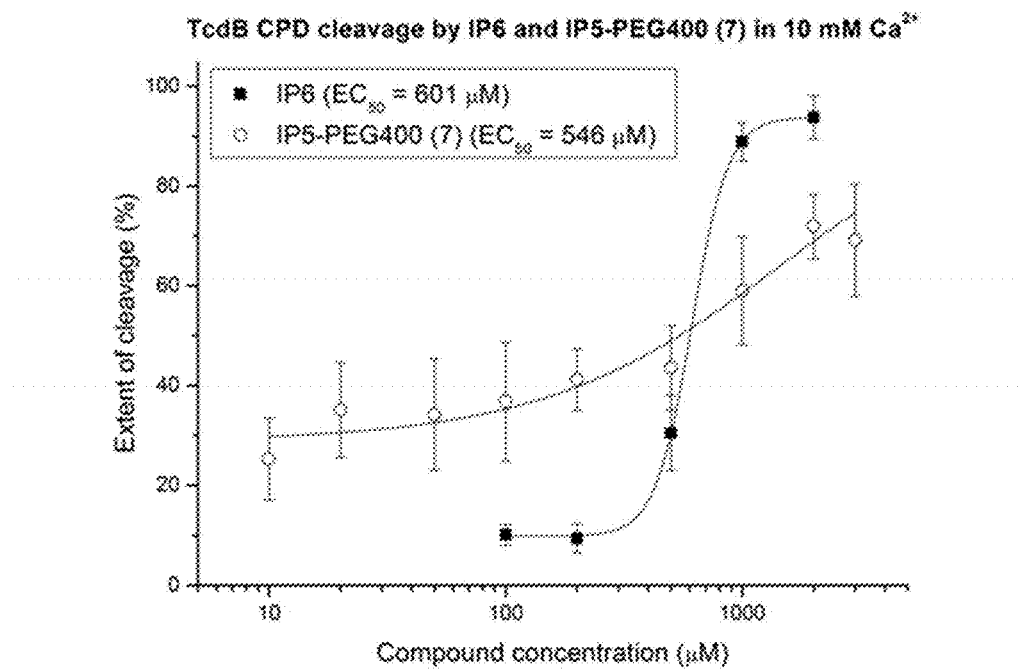
FIG. 1 shows the concentration dependence of cleavage of TcdB cysteine protease domain in the presence of activator compound (7) (empty circles) or IP6 in vitro (1A), and the corresponding kinetics (1B) in 10 mM $Ca^{2+}$.
Figure 1:
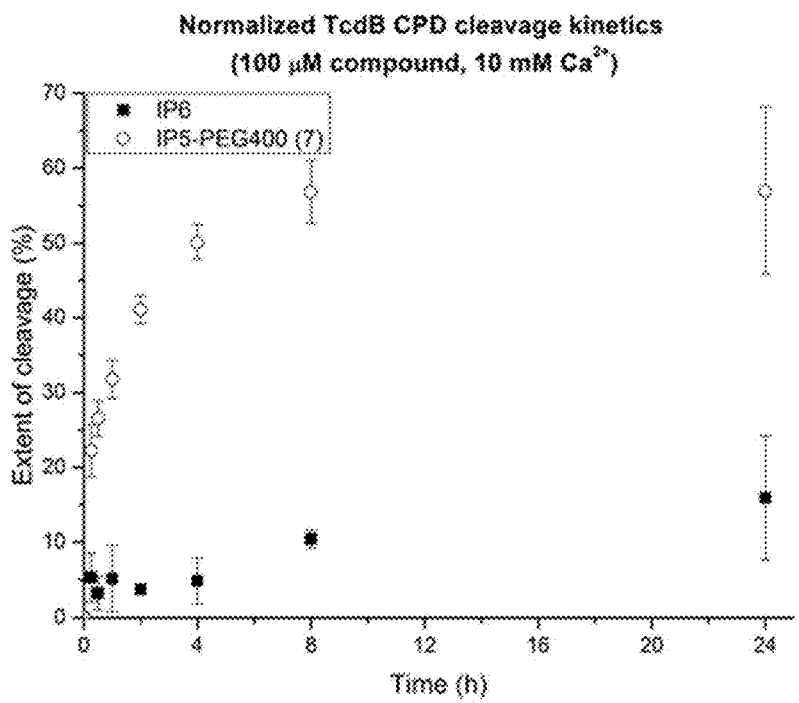
Figure 2:
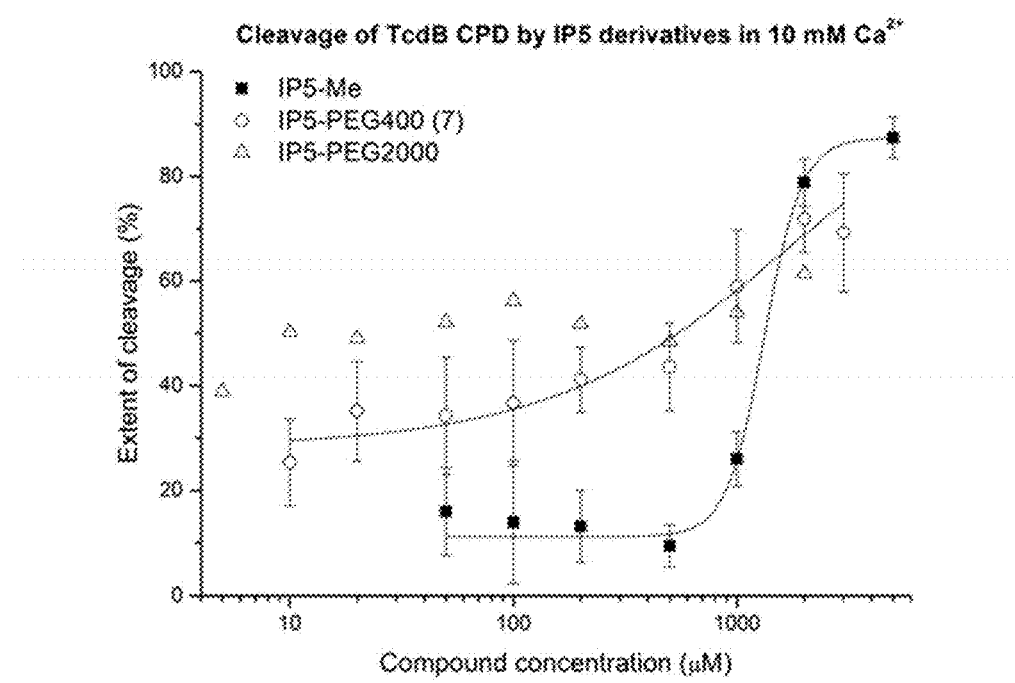
FIG. 2 shows the concentration dependence of cleavage of TcdB cysteine protease domain in the presence of activator compound (7) (empty circles), its PEG2000 analogue (empty triangles), and its methyl analogue (black squares).

The results of this assay for IP6 and compound (7) are shown in FIG. 1A. These demonstrate that 50% the cleavage of toxin fragment is achieved at similar concentrations of IP6 and (7). The activity of IP6 disappears almost completely at 100 µM whereas (7) retains residual activity. The PEG chain of (7) likely confers the molecule with a wider window of solubility.

3. Comparison of Cleavage Kinetics

The compound to be tested was added to the His-tagged cysteine protease domain of *C. difficile* toxin B (same sequence as given above) in presence of 10 mM Ca$^{2+}$ in 100 mM Tris pH 7.4 and incubated for 24 h at 37° C., with aliquots removed at regular intervals. Cleaved protein fragments were separated, visualized and analyzed as indicated above. The results of this assay for IP6 and compound (7) are shown in FIG. 1B. They demonstrate that the extent of cleavage after 4 h is 5-fold higher with (7) than with IP6.

4. Synthesis of Compound (16a-b)

Compound F: A solution of 2,4,6-tri-O-(4-methoxybenzyl)-myo-inositol (E) [D. Lampe, C. Liu, B. V. L. Potter, *J. Med. Chem.* 1994, 37, 907] (0.541 g, 1 mmol, 1 eq.) in dry CH$_2$Cl$_2$ (20 ml, 0.05 m) under an atmosphere of nitrogen was treated with tetrazole in acetonitrile 0.45 m (20.0 ml, 9.0 mmol, 9 eq.) and o-xylylene-N,N-diethylphosphoramidite (6 mmol, 1.44 g, 6 eq.). The reaction mixture was stirred at r.t. for 2 days. A solution of mCPBA (12 mmol, 2.07 g, 12 eq.) dried over Na$_2$SO$_4$ was added at −10° C. and the reaction mixture was stirred at r.t. for an additional 45 min. The mixture was then diluted in EtOAc, washed with a saturated solution of aqueous NaHCO$_3$ and with brine. The organic phase was dried over Na$_2$SO$_4$, filtered and concentrated in vacuo. Purification by flash chromatography (SiO$_2$, CH$_2$Cl$_2$/MeOH gradually from 0% to 4%, three times) afforded 2,4,6-tri-O-(4-methoxybenzyl)-1,3,5-tri-O-(o-xylylenephospho)myo-inositol (F) as a white solid (98%). $^1$H NMR (400 MHz, CDCl$_3$) δ (ppm) 7.28-7.36 (12H, m), 7.19-7.22 (2H, m), 7.12-7.17 (4H, m), 6.86 (2H, d, J 8.5 Hz), 6.71 (4H, d, J 8.5 Hz), 5.25 (1H, d, J 13.6 Hz), 5.21 (1H, d, J 13.6 Hz), 5.15 (1H, d, J 13.7 Hz), 5.11 (1H, d, J 13.7 Hz), 4.91-5.08 (8H, m), 4.83-4.89 (4H, m), 4.69-4.61 (3H, m), 4.57 (1H, q, J 9.2 Hz), 4.38 (2H, ddd, J 2.4, 8.1, 9.5 Hz), 4.10 (2H, t, J 9.5 Hz), 3.78 (3H, s), 3.72 (6H, s); $^{13}$C NMR (125 MHz, CDCl$_3$) δ (ppm) 159.3, 159.1, 135.4, 135.3, 135.2, 130.8, 130.3, 129.7, 129.6, 129.2, 129.13, 129.12, 129.0, 128.9, 128.6, 113.74, 113.57, 80.6 (d, J$_{CP}$ 6.0 Hz), 78.1 (dd, J$_{CP}$ 6.9, 3.2 Hz) 77.6, 77.1 (m), 76.0, 74.9, 68.8, 68.70, 68.68, 68.62, 68.34, 68.28, 55.4, 55.3; $^{31}$P NMR (160 MHz, $^1$H-decoupled, CDCl$_3$) δ (ppm) 1.10, −1.32.

Compound G: Compound F (97 mg, 0.089 mmol) was dissolved in 1 mL dichloromethane. Added 6 mL of a 5:1 mixture of trifluoroacetic acid-water. Stirred 25 min and then diluted with 10 mL toluene and concentrated under vacuum. The resulting residue was triturated with hexane and dichloromethane and then dried under high vacuum. Yielded 68 mg of crude compound G that was used directly in the next step.

Compound H: Compound G (39 mg, 0.054 mmol) was dissolved in 3 mL DMF and SO$_3$.Et$_3$N (195 mg, 1.07 mmol) was added. The solution was stirred overnight at 50° C. and concentrated on a rotavap. The residue was dissolved in 6 mL water, filtered and loaded on three Vac 6 cc 1 g tC18 Sep-Pak cartridges (Waters). The columns were eluted with a gradient from 0-40% MeOH/H$_2$O. Yielded 32 mg of H. $^1$H NMR (400 MHz; MeOD): δ 7.45-7.40 (m, 4H), 7.39-7.33 (m, 4H), 7.28-7.24 (m, 2H), 7.21-7.19 (m, 2H), 5.69-5.60 (m, 4H), 5.47 (dd, J=13.2, 10.4 Hz, 2H), 5.41 (t, J=2.9 Hz, 2H), 5.40-5.35 (m, 2H), 5.20-5.16 (m, 1H), 5.11-4.97 (m, 5H), 4.90-4.81 (m, 2H), 3.24 (q, J=7.3 Hz, 17H), 1.32 (t, J=7.3 Hz, 25H). $^{13}$C NMR (101 MHz; MeOD/CDCl$_3$): δ 131.6, 131.2, 125.26, 125.21, 125.09, 124.93, 124.87, 124.78, 70.25, 70.22, 70.19, 69.95, 69.90, 65.18, 65.11, 65.07, 65.00, 64.85, 64.78, 42.4, 4.2; $^{31}$P NMR (162 MHz; MeOD/CDCl$_3$): δ −7.8, −8.9

Compound PSPSPS ((16a)b): Compound H (32 mg) was dissolved in 3 mL H$_2$O. A small scoop of Pd on activated carbon (10%) was added, the mixture was placed under a H$_2$ atmosphere and stirred for 4 h. The mixture was then purged with N2 and a drop of NH$_4$OH was added. The mixture was filtered though celite and evaporated on a rotavap. The residue was dissolved in 1 mL water, loaded on a Vac 6 cc 1 g tC18 Sep-Pak cartridge (Waters) and eluted with water. The eluted fractions were lyophilized and analyzed by 1H NMR. Yielded 16 mg of PSPSPS.2Et$_3$NH$^+$.xNH$_4^+$. $^1$H-NMR (400 MHz; D$_2$O): δ 4.93-4.78 (m, 3H), 4.55-4.39 (m, 3H), 3.13 (q, J=7.3 Hz, 14H), 1.21 (t, J=7.3 Hz, 21H). $^{31}$P NMR (162 MHz; D$_2$O): δ −0.3, −0.7.

The cleavage induced by compound PSPSPS ((16a-b) was determined in the presence of calcium as described in example 2 and the result is shown in FIG. 7. The cleavage induced by this derivative was 50% at a concentration of 20 μM, which is more efficient than IP6 (601 μM). This result shows that the presence of some sulfate groups enhances the activity of the compound in the presence of calcium.

The invention claimed is:

1. A method for treating a *C. difficile* infection, comprising administering to a subject a composition comprising a compound described by general formula (16a) or (16b):

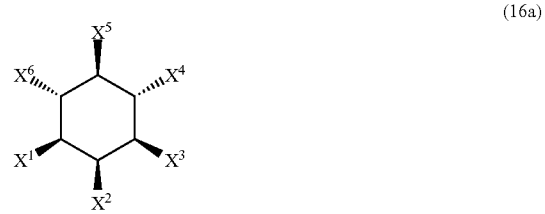

(16a)

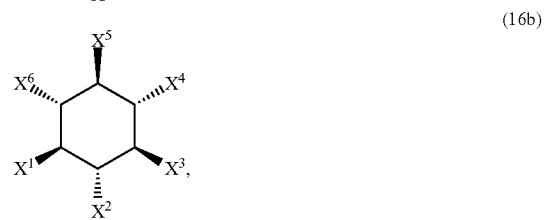

(16b)

wherein
a) $X^2$ is OSO$_3^-$, and $X^1$, $X^3$, $X^4$, $X^5$ and $X^6$ are each independently selected from OPO$_3^{2-}$, OPSO$_2^{2-}$ or OSO$_3^-$;
b) $X^1$, $X^3$ and $X^5$ are OPO$_3^{2-}$ and $X^2$, $X^4$ and $X^6$ are OSO$_3^-$
c) $X^1$, $X^3$ and $X^5$ are OSO$_3^-$ and $X^2$, $X^4$ and $X^6$ are OPO$_3^{2-}$
d) $X^4$, $X^5$ and $X^6$ are OSO$_3^-$ and $X^1$, $X^2$ and $X^3$ are OPO$_3^{2-}$,
e) $X^4$, $X^5$ and $X^6$ are OPO$_3^{2-}$ and $X^1$, $X^2$ and $X^3$ are OSO$_3^-$ or
f) $X^2$ and $X^5$ are OPO$_3^{2-}$ and $X^1$, $X^3$, $X^4$, and $X^6$ are OSO$_3^-$,
g) $X^2$ and $X^5$ are OSO$_3^-$ and $X^1$, $X^3$, $X^4$, and $X^6$ are OPO$_3^{2-}$,
h) $X^2$ and $X^3$ are OPO$_3^{2-}$ and $X^1$, $X^4$, $X^5$, and $X^6$ are OSO$_3^-$, or
i) $X^2$ and $X^3$ are OSO$_3^-$ and $X^1$, $X^4$, $X^5$, and $X^6$ are OPO$_3^{2-}$.

2. The method of claim 1, wherein the composition further comprises an antibiotic.

3. The method of claim 2, wherein the antibiotic is metronidazole, vancomycin or fidaxomicin.

* * * * *